(12) United States Patent
Weiner et al.

(10) Patent No.: US 9,333,496 B2
(45) Date of Patent: *May 10, 2016

(54) COBALT/TIN CATALYST FOR PRODUCING ETHANOL

(75) Inventors: Heiko Weiner, Pasadena, TX (US);
Zhenhua Zhou, Houston, TX (US);
Radmila Jevtic, Pasadena, TX (US);
Victor J. Johnston, Houston, TX (US)

(73) Assignee: CELANESE INTERNATIONAL CORPORATION, Irving, TX (US)

(*) Notice: Subject to any disclaimer, the term of this patent is extended or adjusted under 35 U.S.C. 154(b) by 393 days.

This patent is subject to a terminal disclaimer.

(21) Appl. No.: 13/408,240

(22) Filed: Feb. 29, 2012

(65) Prior Publication Data

US 2013/0225878 A1    Aug. 29, 2013

(51) Int. Cl.
| | |
|---|---|
| *B01J 23/75* | (2006.01) |
| *B01J 23/835* | (2006.01) |
| *B01J 37/08* | (2006.01) |
| *C07C 29/149* | (2006.01) |
| *B01J 37/02* | (2006.01) |
| *B01J 23/00* | (2006.01) |
| *B01J 23/89* | (2006.01) |

(52) U.S. Cl.
CPC ............... *B01J 37/08* (2013.01); *B01J 23/002* (2013.01); *B01J 23/835* (2013.01); *B01J 23/8966* (2013.01); *B01J 37/0205* (2013.01); *B01J 37/0213* (2013.01); *C07C 29/149* (2013.01); *B01J 2523/00* (2013.01)

(58) Field of Classification Search
CPC combination set(s) only.
See application file for complete search history.

(56) References Cited

U.S. PATENT DOCUMENTS

| | | | |
|---|---|---|---|
| 2,607,807 A | 8/1952 | Ford | |
| 2,744,939 A | 5/1956 | Kennel | |
| 3,102,150 A | 8/1963 | Hunter et al. | |
| 3,478,112 A | 11/1969 | Karl et al. | |
| 3,864,284 A | 2/1975 | Clippinger et al. | |
| 3,960,710 A * | 6/1976 | Pollitzer et al. | 208/139 |
| 3,990,952 A | 11/1976 | Katzen et al. | |
| 4,317,918 A | 3/1982 | Takano et al. | |
| 4,395,576 A | 7/1983 | Kwantes et al. | |
| 4,398,039 A | 8/1983 | Pesa et al. | |
| 4,399,305 A | 8/1983 | Schreck et al. | |
| 4,421,939 A | 12/1983 | Kiff et al. | |
| 4,443,639 A | 4/1984 | Pesa et al. | |
| 4,476,326 A | 10/1984 | Lin et al. | |
| 4,480,115 A | 10/1984 | McGinnis | |
| 4,514,515 A | 4/1985 | Travers et al. | |
| 4,517,391 A | 5/1985 | Schuster et al. | |
| 4,550,185 A | 10/1985 | Mabry et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,985,572 A | 1/1991 | Kitson et al. | |
| 4,990,655 A | 2/1991 | Kitson et al. | |
| 5,008,235 A | 4/1991 | Wegman et al. | |
| 5,061,671 A | 10/1991 | Kitson et al. | |
| 5,124,004 A | 6/1992 | Grethlein et al. | |
| 5,137,861 A | 8/1992 | Shih et al. | |
| 5,144,068 A | 9/1992 | Smith et al. | |
| 5,149,680 A | 9/1992 | Kitson et al. | |
| 5,155,084 A | 10/1992 | Horn et al. | |
| 5,243,095 A | 9/1993 | Roberts et al. | |
| 5,350,504 A | 9/1994 | Dessau | |
| RE35,377 E | 11/1996 | Steinberg et al. | |
| 5,821,111 A | 10/1998 | Grady et al. | |
| 5,945,570 A | 8/1999 | Arhancet et al. | |
| 6,049,008 A | 4/2000 | Roberts et al. | |
| 6,204,417 B1 | 3/2001 | Fischer et al. | |
| 6,232,352 B1 | 5/2001 | Vidalin et al. | |
| 6,294,703 B1 | 9/2001 | Hara et al. | |
| 6,462,231 B1 | 10/2002 | Yanagawa et al. | |
| 6,495,730 B1 | 12/2002 | Konishi et al. | |
| 6,509,180 B1 | 1/2003 | Verser et al. | |
| 6,632,330 B1 | 10/2003 | Colley et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,906,228 B2 | 6/2005 | Fischer et al. | |
| 6,927,048 B2 | 8/2005 | Verser et al. | |
| 7,084,312 B1 | 8/2006 | Huber et al. | |
| 7,208,624 B2 | 4/2007 | Scates et al. | |
| 7,297,236 B1 | 11/2007 | Vander Griend et al. | |

(Continued)

FOREIGN PATENT DOCUMENTS

| | | |
|---|---|---|
| EP | 0104197 | 4/1984 |
| EP | 0137749 | 4/1985 |

(Continued)

OTHER PUBLICATIONS

DeOliveira Vigier et al. Journal of Molecular Catalysis A Chemical 306 (2009) 102-106.*
Pouilloux et al. Catalysis Today 63 (2000) 87-100.*
K. DeOliveira et al. Journal of Catalysis 204, 230-237 (2001). (8 pages).*
International Search Report and Written Opinion for PCT/US2012/071355 mailed Apr. 5, 2013.
Pestman et al., Reactions of Carboxylic Acids on Oxides, Journal of Catalysis 168:255-264 (1997).
T. Yokoyama, et al., "Carboxylic Acids and Derivatives", Fine Chemicals through Heterogenous Catalysis, pp. 370-379.
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).
Pestman et al., Identification of the Active Sites in the Selective Hydrogenation of Acetic Acid to Acetaldehyde on Iron Oxide Catalysts, Journal of Catalysis 174:142-152 (1998).

(Continued)

*Primary Examiner* — Nyeemah A Grazier
(74) *Attorney, Agent, or Firm* — Kilpatrick Townsend & Stockton LLP

(57) ABSTRACT

The present invention relates to a process for the formation of alcohols from alkanoic acids, the steps of the process comprising: contacting a feed stream containing the alkanoic acid and hydrogen at an elevated temperature with a hydrogenating catalyst comprising from 3 to 25 wt. % of active metals on a support, wherein the active metals comprise cobalt and tin.

11 Claims, No Drawings

(56) References Cited

U.S. PATENT DOCUMENTS

| | | | |
|---|---|---|---|
| 7,375,049 | B2 | 5/2008 | Hayes et al. |
| 7,425,657 | B1 | 9/2008 | Elliott et al. |
| 7,507,562 | B2 | 3/2009 | Verser et al. |
| 7,538,060 | B2 | 5/2009 | Barnicki et al. |
| 7,553,397 | B1 | 6/2009 | Colley et al. |
| 7,572,353 | B1 | 8/2009 | Vander Griend et al. |
| 7,608,744 | B1 | 10/2009 | Johnston et al. |
| 7,682,812 | B2 | 3/2010 | Verser et al. |
| 7,863,489 | B2 | 1/2011 | Johnston et al. |
| 7,884,253 | B2 | 2/2011 | Stites et al. |
| 8,071,821 | B2 | 12/2011 | Johnston et al. |
| 8,080,694 | B2 | 12/2011 | Weiner et al. |
| 8,309,772 | B2 | 11/2012 | Weiner et al. |
| 8,455,702 | B1 * | 6/2013 | Zhou et al. ............. 568/885 |
| 8,471,075 | B2 | 6/2013 | Johnston et al. |
| 8,501,652 | B2 | 8/2013 | Johnston et al. |
| 2003/0077771 | A1 | 4/2003 | Verser et al. |
| 2003/0104587 | A1 | 6/2003 | Verser et al. |
| 2004/0195084 | A1 | 10/2004 | Hetherington et al. |
| 2006/0019360 | A1 | 1/2006 | Verser et al. |
| 2006/0127999 | A1 | 6/2006 | Verser et al. |
| 2007/0265360 | A1 | 11/2007 | Luo et al. |
| 2007/0270511 | A1 | 11/2007 | Melnichuk et al. |
| 2008/0207953 | A1 | 8/2008 | Houssin et al. |
| 2009/0023192 | A1 | 1/2009 | Verser et al. |
| 2009/0166172 | A1 | 7/2009 | Casey et al. |
| 2009/0221725 | A1 | 9/2009 | Chorney et al. |
| 2009/0318573 | A1 | 12/2009 | Stites et al. |
| 2009/0326080 | A1 | 12/2009 | Chornet et al. |
| 2010/0016454 | A1 | 1/2010 | Gracey et al. |
| 2010/0029980 | A1 | 2/2010 | Johnston et al. |
| 2010/0029995 | A1 | 2/2010 | Johnston et al. |
| 2010/0029996 | A1 | 2/2010 | Danjo et al. |
| 2010/0121114 | A1 | 5/2010 | Johnston et al. |
| 2010/0196789 | A1 | 8/2010 | Fisher et al. |
| 2010/0197484 | A1 * | 8/2010 | Sala et al. ............. 502/178 |
| 2010/0197485 | A1 | 8/2010 | Johnston et al. |
| 2010/0197985 | A1 | 8/2010 | Johnston et al. |
| 2010/0249479 | A1 | 9/2010 | Berg-Slot et al. |
| 2010/0273229 | A1 | 10/2010 | Verser et al. |
| 2011/0004033 | A1 | 1/2011 | Johnston et al. |
| 2011/0046421 | A1 | 2/2011 | Daniel et al. |
| 2011/0060169 | A1 | 3/2011 | Kaizik et al. |
| 2011/0098501 | A1 | 4/2011 | Johnston et al. |
| 2011/0190117 | A1 | 8/2011 | Weiner et al. |
| 2011/0263891 | A1 | 10/2011 | Weiner et al. |
| 2011/0263911 | A1 | 10/2011 | Johnston et al. |
| 2012/0016042 | A1 * | 1/2012 | Maury et al. ............. 518/721 |
| 2012/0238785 | A1 | 9/2012 | Zhou et al. |
| 2012/0245022 | A1 | 9/2012 | Weiner et al. |
| 2013/0072728 | A1 | 3/2013 | Weiner et al. |
| 2013/0131399 | A1 * | 5/2013 | Weiner et al. ............. 568/885 |
| 2013/0231510 | A1 | 9/2013 | Johnston et al. |
| 2013/0245332 | A1 * | 9/2013 | Weiner et al. ............. 568/885 |
| 2013/0245335 | A1 * | 9/2013 | Zhou et al. ............. 568/885 |
| 2013/0324623 | A1 * | 12/2013 | Maury et al. ............. 518/719 |
| 2013/0324624 | A1 * | 12/2013 | Maury et al. ............. 518/719 |
| 2013/0336878 | A1 * | 12/2013 | Johnson ............. 423/648.1 |
| 2014/0031546 | A1 * | 1/2014 | Shen et al. ............. 544/257 |

FOREIGN PATENT DOCUMENTS

| | | |
|---|---|---|
| EP | 0167300 | 1/1986 |
| EP | 0175558 | 3/1986 |
| EP | 0285420 | 10/1988 |
| EP | 0372847 | 6/1990 |
| EP | 0990638 | 4/2000 |
| EP | 1262234 | 12/2002 |
| EP | 1277826 | 1/2003 |
| EP | 2186787 | 5/2010 |
| GB | 1168785 | 10/1969 |
| GB | 1559540 | 1/1980 |
| GB | 2136704 | 9/1984 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 2005/102513 | 11/2005 |
| WO | WO 2009/063176 | 5/2009 |
| WO | 2009/077720 A1 | 6/2009 |
| WO | 2009/077729 A1 | 6/2009 |
| WO | WO 2009/086839 | 7/2009 |
| WO | WO 2009/105860 | 9/2009 |
| WO | 2010/014153 A2 | 2/2010 |
| WO | 2010/014151 A2 | 4/2010 |
| WO | WO 2010/055285 | 5/2010 |
| WO | 2011/053365 A1 | 5/2011 |
| WO | WO 2011/056595 | 5/2011 |
| WO | WO 2011094713 A1 * | 8/2011 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordonez et al., The role of metal and support sites on the hydrogenation of acetic acid on Ru-based catalysts, 21st NAM San Francisco, CA, Jun. 10, 2009.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Proc. Roy Soc. A314, pp. 473-498 (1970).

Gursahani et al., Reaction kinetics measurements and analysis of reaction pathways for conversions of acetic acid, ethanol, and ethyl acetate over silica-supported Pt, Applied Catalysis A: General 222 (2001) 369-392.

* cited by examiner

COBALT/TIN CATALYST FOR PRODUCING ETHANOL

FIELD OF THE INVENTION

The present invention relates to cobalt and tin catalysts, to processes for making such catalysts, and to processes for reducing alkanoic acids using the catalyst. In one embodiment, ethanol may be produced by reducing acetic acid in the presence of a catalyst containing cobalt and tin.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

In a first embodiment, the invention is directed to a hydrogenation catalyst for reducing alkanoic acids to alcohols, the catalyst comprising from 3 to 25 wt. % of active metals on a support, wherein the active metals comprise cobalt and tin. In some embodiments, the active metals are present from 5 to 20 wt. % in a molar ratio from 1.2:1 to 1:1.2. The support further comprises a support modifier present fro 0.1 to 50 wt. %. The catalyst may comprise less than 2 wt. % of nickel, iron, ruthenium, rhodium, palladium, osmium, iridium or platinum. The catalyst is free of copper and/or zinc.

In a second embodiment, the invention is directed to a hydrogenation catalyst for reducing alkanoic acids to alcohols, the catalyst comprising cobalt, tin, and a metal selected from the group consisting of nickel, iron, ruthenium, rhodium, palladium, osmium, iridium, and platinum on a support, wherein the metal is present in an amount of less than 2 wt. %. The substantially equal molar ratio is from 1.2:1 to 1:1.2.

In a third embodiment, the invention is directed to a hydrogenation catalyst for reducing alkanoic acids to alcohols, the catalyst comprising from 3 to 25 wt. % of active metals on a support, wherein the active metals comprise a substantially equal molar ratio of cobalt to tin.

In a fourth embodiment, the invention is directed to a process for formation of ethanol from acetic acid comprising contacting a feed stream containing acetic acid and hydrogen at an elevated temperature with a hydrogenating catalyst comprising from 3 to 25 wt. % of active metals on a support, wherein the active metals comprise cobalt and tin. In some embodiments, the active metals are present from 5 to 20 wt. % in a molar ratio from 1.2:1 to 1:1.2. The support comprises a support modifier present from 0.1 to 50 wt. %. The feed stream may be produced by gasifying a oil, coal, natural gas and/or biomass. The acetic acid selectivity to ethanol is greater than 60%. Ethanol is separated in one or more columns after the hydrogenation to produce a finished ethanol product.

In a fifth embodiment, the invention is directed to a process for formation of ethanol from acetic acid comprising contacting a feed stream containing acetic acid and hydrogen at an elevated temperature with a hydrogenating catalyst comprising from 3 to 25 wt. % of active metals on a support, wherein the active metals comprise a substantially equal molar ratio of cobalt to tin.

In a sixth embodiment, the invention is directed to a process for formation of ethanol from acetic acid comprising contacting a feed stream containing acetic acid and hydrogen at an elevated temperature with a hydrogenating catalyst comprising cobalt, tin, and a metal selected from the group consisting of nickel, iron, ruthenium, rhodium, palladium, osmium, iridium, and platinum on a support, wherein the metal is present in an amount of less than 2 wt. %.

DETAILED DESCRIPTION OF THE INVENTION

Introduction

In general, this invention relates to a catalyst for reducing alkanoic acids, and preferably for reducing acetic acid. The catalyst comprises active metals on a support. The active metals comprise cobalt and tin. Without being bound by theory, the presence of tin in the catalyst may promote the activity of the catalyst to convert acetic acid, increase selectivity to ethanol, and stabilize the catalyst over a longer period of use. Tin, which demonstrates poor hydrogenation abilities when used alone, surprisingly and unexpectedly may increase the performance of catalyst comprise cobalt. In addition, the combination of cobalt and tin surprisingly and advantageously produces a low selectivity for methane. Thus, the bimetallic combination of cobalt and tin is advantageous in producing ethanol from acetic acid.

In preferred embodiments, the total metal loading is from 3 to 25 wt. %, and more preferably from 5 to 20 wt. % or 10 to 20 wt. %. In some embodiments, cobalt may be present in an amount of at least 1.5 wt %, e.g., at least 3 wt. %. When the metal loading is lower, the acetic acid conversion may be reduced. Cobalt and/or tin may be present on the catalyst as an oxide. In one embodiment the molar ratio of cobalt and tin may be from 1.9:1 to 1:1.9, e.g. from 1.5:1 to 1:1.5, or from 1.4:1 to 1:1.4. In a more preferred embodiment there may be a substantially equal molar ratio of cobalt and tin on a support, that is, in a molar ratio from 1.2:1 to 1:1.2 and more preferably a molar ratio of 1:1.

In some embodiments, there may be additional active metals that may be used in combination with cobalt/tin catalyst. Exemplary additional active metals include nickel, iron, ruthenium, rhodium, palladium, osmium, iridium, and platinum. In one embodiment, embodiment, the additional active metal is platinum. When present, the additional active metal is preferably less than the total metal loading of cobalt and tin. In one embodiment, the metal loading of the active metal is less than 2 wt. %, e.g., less than 1.75 wt. % or less than 1.5 wt. %. In terms of the ranges, the metal loading of the active metal is from 0.4 wt. % to 1 wt. %, e.g., from 0.4 wt. % to 0.7 wt. % or from 0.4 wt. % to 0.6 wt. %. In one preferred embodiment, the cobalt/tin catalyst does not contain any copper or zinc.

Support

The catalysts of the present invention may be on any suitable support. In one embodiment, the support may be an inorganic oxide. In one embodiment, the support may be selected from the group consisting of silica, silica/alumina, calcium metasilicate, pyrogenic silica, high purity silica, carbon, alumina, titania, zirconia, graphite, zeolites, and mixtures thereof. In another embodiment, the support may be selected from the group consisting of silica, silica/alumina, calcium metasilicate, pyrogenic silica, high purity silica, carbon, alumina, and mixtures thereof. Preferably, the support comprises silica. In one embodiment, the support is present in an amount from 25 wt. % to 97 wt. %, e.g., from 30 wt. % to 95 wt. % or from 35 wt. % to 80 wt. %.

The surface area of silicaceous support, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the silicaceous support preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support, and hence of the resulting catalyst composition, may vary widely. In some exemplary embodiments, the morphology of the support and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support has a morphology that allows for a packing density of from 0.1 to 1.0 $g/cm^3$, e.g., from 0.2 to 0.9 $g/cm^3$ or from 0.3 to 0.8 $g/cm^3$. In terms of size, the silica support preferably has an average particle size, e.g., meaning the diameter for spherical particles or equivalent spherical diameter for non-spherical particles, of from 0.01 to 1.0 cm, e.g., from 0.1 to 0.7 cm or from 0.2 to 0.5 cm. Since the one or more active metal(s) that are disposed on or within the support are generally very small in size, those active metals should not substantially impact the size of the overall catalyst particles. Thus, the above particle sizes generally apply to both the size of the support as well as to the final catalyst particles.

A preferred silica support is SS61138 High Surface Area (HSA) Silica Catalyst Carrier from Saint-Gobain N or Pro. The Saint-Gobain N or Pro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$.

A preferred silica/alumina support is KA-160 (Süd Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

Support Modifiers

The support may also comprise a support modifier. In one embodiment, the total weight of the support modifiers are present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Support modifiers may adjust the acidity of the support. For example, the acid sites, e.g. Brønsted acid sites, on the support may be adjusted by the support modifier to favor selectivity to ethanol during the hydrogenation of acetic acid. The acidity of the support may be adjusted by reducing the number or reducing the availability of Brønsted acid sites on the support. The support may also be adjusted by having the support modifier change the pKa of the support. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In particular, the use of modified supports that adjusts the acidity of the support to make the support less acidic or more basic favors formation of ethanol over other hydrogenation products.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include those selected from the group consisting of $WO_3$, $MoO_3$, $Fe_2O_3$, $Cr_2O_3$, $V_2O_5$, $Nb_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be crystalline or amorphous.

Process to Make Catalyst

The present invention also relates to processes for making the catalyst. One or more support modifiers, if desired, may also be added to the support by mixing or through impregnation. Powdered materials of the modified supports or a precursor thereto may pelletized, crushed and sieved and added to the support. The use of a solvent, such as water, glacial acetic acid, a strong acid such as hydrochloric acid, nitric acid, or sulfuric acid, or an organic solvent, may be preferred. The resulting mixture may be stirred and added to additional support using, for example, incipient wetness techniques in which the precursor to the support modifier is added to a support having the same pore volume as the volume of the solution. Capillary action then draws the precursor to the support modifier into the pores in the support. The support containing precursor to the support modifier can then be formed by drying to drive off water and any volatile components within the support solution and depositing the tin on the support. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours.

Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support into desired size distribution can be employed.

In a preferred method of preparing the catalyst, cobalt and tin are impregnated onto the support. A precursor of the active metals preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second active metal precursor also preferably is impregnated into the support from a second metal precursor.

Impregnation occurs by adding, optionally drop wise, either or both the first metal precursor and/or the second metal precursor and/or additional metal precursors, preferably in suspension or solution, to the dry support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the active metal onto the support may occur simultaneously (co-impregnation) or sequentially. In simultaneous impregnation, the active metal precursors are mixed together and added to the support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first active metal precursor is first added to the support followed by drying and calcining, and the resulting material is then impregnated with the second active metal precursor followed by an additional drying and calcining step to form the final catalyst composition.

Suitable metal precursors include, for example, metal halides, amine solubilized metal hydroxides, metal nitrates or metal oxalates. For example, suitable compounds for tin precursors and cobalt precursors include potassium stannate, sodium stannate, stannic chloride, stannous chloride, stannous nitrate, stannous oxalate, and cobalt nitrate hexahydrate. Generally, both from the point of view of economics and environmental aspects, aqueous solutions of soluble compounds are preferred. A particularly preferred precursor to tin is stannous oxalate, $SnC_4H_4O_6.xH_2O$. A particularly preferred precursor to cobalt is cobalt nitrate hexahydrate, $Co(NO_3)_2.6H_2O$. Calcining of the solution with the support and active metal may occur, for example, at a temperature of from 250° C. to 800° C., e.g., from 300° C. to 700° C. or from 350° C. to 500° C., optionally for a period of from 1 to 12 hours, e.g., from 2 to 10 hours, from 4 to 8 hours or about 6 hours.

In one aspect, the tin precursor is first added to the support, followed by the cobalt metal precursor. Of course the reverse order of addition is also possible. As indicated above, in the sequential embodiment, each impregnation step preferably is followed by drying and calcination. In those cases where substantially pure ethanol is to be produced, it is generally preferable to use nitrogenous amine and/or nitrate based precursors.

Use of Catalyst to Hydrogenate Acetic Acid

In one embodiment there is a process for producing ethanol by reducing alkanoic acid, and more preferable acetic acid, in the presence of the catalyst. The hydrogenation reaction may be represented as follows:

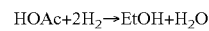

The raw materials, acetic acid, ethyl acetate and hydrogen, fed to the primary reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, from 100 kPa to 2100 kPa, or from 200 kPa to 2100 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid, respectively. Conversion is expressed as a percentage based on acetic acid in the feed. The conversion of acetic acid may be at least 10%, e.g., at least 20%, at least 40%, at least 50%, at least 60%, at least 70% or at least 80%. Although catalysts that have high conversions are desirable, especially acetic acid conversions that are at least 80% or at least 90%, in some embodiments a low acetic acid conversion may be acceptable at high selectivity for ethanol. It is, of course, well understood that in many cases, it is possible to compensate for low acetic acid conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst have a selectivity to ethanol is at least 50%, e.g., at least 60%, or at least 70%. Preferably, the selectivity to ethanol may be high and is at least 75%, e.g., at least 80% or at least 85%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 0 to 20 | 1 to 12 | 3 to 10 |

TABLE 1-continued

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 97 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the procedures used for the preparation of various catalysts employed in the process of this invention.

EXAMPLES

Example A

Preparation of 50 Mol. % Cobalt and 50 Mol. % Tin on Silica

Silica (1.0 g) of uniform particle size distribution was dried at 120° C. in an oven under nitrogen atmosphere overnight and then cooled to room temperature to form the support material. A preferred silica support material is SS61138 High Surface Area (HSA) Silica Catalyst Carrier from Saint-Gobain N or Pro. A stock solution of 0.5 $g_{salt}$/mL, of Co$(NO_3)_2 \cdot 6H_2O$ (Alfa Aesar) in 8M nitric acid was prepared. A stock solution of 0.25 $g_{salt}$/mL, of Sn in 8M nitric acid was prepared with $SnC_4H_4O_6 \cdot xH_2O$ (Alfa Aesar). 193.05 µL of the stock cobalt solution, 1060.4 µL of the stock tin solution and 66.55 µL of nitric acid was prepared and 1200 µL of this mixture was impregnated on 1 g of the support. The impregnation of the active metals was repeated so that the total active metal loading was 20 wt. %. Co and Sn were added in equal molar amounts. The impregnated catalyst was dried at 50° C. in air with a ramp rate of 1° C./minute, followed by a ramp rate of 2° C./minute up to 120° C. The catalyst was kept at 120° C. for 2 hours and then calcined at 450° C. for four hours with a 2° C./minute heating rate in air.

Example B

Preparation of 50 Mol. % Cobalt and 50 Mol. % Tin on Silica-Alumina

Silica-alumina (1.0 g) of uniform particle size distribution was dried at 120° C. in an oven under nitrogen atmosphere overnight and then cooled to room temperature. The support contained 13.4 wt. % $Al_2O_3$. 457.6 µL of the stock cobalt solution from Example A, 564.3 µL of the stock tin solution from Example A and 518.1 µL of water was prepared and this mixture was impregnated on 1 g of the silica-alumina support. The impregnation was repeated so that the total active metal loading of cobalt and tin was 20 wt. %. The drying and calcining of Example A was repeated for this catalyst material.

Example C

Comparative

Preparation of 100 Mol. % Cobalt on Silica

Silica (1.0 g) of Example A was used. A stock solution of 0.5 $g_{salt}$/mL of Co$(NO_3)_2 \cdot 6H_2O$ (Alfa Aesar) in 8M nitric acid was prepared. 193.05 µL of the stock cobalt solution and 66.55 µL of nitric acid was prepared and 1200 µL of this mixture was impregnated on 1 g of the support. The impregnation of cobalt was repeated so that the total metal loading was 20 wt. %. The drying and calcining of Example A was repeated for this catalyst material.

Example D

Comparative

Preparation of 100 Mol. % Cobalt on Silica-Alumina

Silica-alumina (1.0 g) of uniform particle size distribution was dried at 120° C. in an oven under nitrogen atmosphere overnight and then cooled to room temperature. A stock solution of 0.5 $g_{salt}$/mL, of Co(NO$_3$)$_2$.6H$_2$O (Alfa Aesar) in 8M nitric acid was prepared. 193.05 µL of the stock cobalt solution and 66.55 µL of nitric acid was prepared and 1200 µL of this mixture was impregnated on 1 g of the silica-alumina support. The impregnation of cobalt was repeated so that the total metal loading was 20 wt. %. The drying and calcining of Example A was repeated for this catalyst material.

Example E

Comparative

Preparation of 50 Mol. % Cobalt and 50 Mol. % Copper on Silica

The catalyst of Example A was repeated, except the tin was replaced with copper and the nitric acid was replaced with water. A stock solutions of 0.5 $g_{salt}$/mL, of Cu(NO$_3$)$_2$.3H$_2$O (Alfa Aesar). 457.6 µL of the stock copper solution was impregnated along with the cobalt on the support. The drying and calcining of Example A was repeated for this catalyst material.

Example F

Comparative

Preparation of 50 Mol. % Cobalt and 50 Mol. % Copper on Silica-Alumina

The catalyst of Example B was repeated, except the tin was replaced with copper and the nitric acid was replaced with water. A stock solutions of 0.5 $g_{salt}$/mL, of Cu(NO$_3$)$_2$.3H$_2$O (Alfa Aesar). 457.6 µL of the stock copper solution was impregnated along with the cobalt on the support. The drying and calcining of Example A was repeated for this catalyst material.

Example G

Preparation of 50 Mol. % Cobalt and 50 Mol. % Tin on Silica-Calcium Metasilicate (10 Wt. %) Support 2.7 g silica and 0.3 g calcium metasilicate of uniform particle size distribution of about 0.2 mm was dried at 120° C. in an oven under nitrogen atmosphere overnight and then cooled to room temperature to form the support. A stock solution of 0.5 $g_{salt}$/mL, of Co(NO$_3$)$_2$.6H$_2$O (Alfa Aesar) in 8M nitric acid was prepared. A stock solution of 0.25 $g_{salt}$/mL, of Sn in 8M nitric acid was prepared with SnC$_4$H$_4$O$_6$.xH$_2$O (Alfa Aesar). 193.05 µL of the stock cobalt solution, 1060.4 µL of the stock tin solution and 66.55 µL of nitric acid was prepared and 1200 µL of this mixture was impregnated on 1 g of the modified support. The impregnation of the active metals was repeated so that the total active metal loading was 20 wt. %. Co and Sn were added in equal molar amounts. The drying and calcining of Example A was repeated for this catalyst material.

Example H

Comparative

Preparation of 75 Mol. % Cobalt and 25 Mol. % Tin on Silica Support

Silica (1.0 g) of Example A was used. A stock solution of 0.5 $g_{salt}$/mL of Co(NO$_3$)$_2$.6H$_2$O (Alfa Aesar) in 8M nitric acid was prepared. A stock solution of 0.25 $g_{salt}$/mL, of Sn in 8M nitric acid was prepared with SnC$_4$H$_4$O$_6$.xH$_2$O (Alfa Aesar). 193.05 µL of the stock cobalt solution, 1060.4 µL of the stock tin solution and 66.55 µL of nitric acid was prepared and 1200 µL of this mixture was impregnated on 1 g of the support. The impregnation of the active metals was repeated so that the total active metal loading was 20 wt. %, with 75 mol. % Co and 25 mol. % Sn. The drying and calcining of Example A was repeated for this catalyst material.

Example I

Comparative

Preparation of 75 Mol. % Cobalt and 25 Mol. % Tin on Silica-Calcium Metasilicate (10 Wt. %) Support The modified support containing calcium metasilicate of Example G was used. A stock solution of 0.5 $g_{salt}$/mL, of Co(NO$_3$)$_2$.6H$_2$O (Alfa Aesar) in 8M nitric acid was prepared. A stock solution of 0.25 $g_{salt}$/mL, of Sn in 8M nitric acid was prepared with SnC$_4$H$_4$O$_6$.xH$_2$O (Alfa Aesar). 193.05 µL of the stock cobalt solution, 1060.4 µL of the stock tin solution and 66.55 µL of nitric acid was prepared and 1200 µL of this mixture was impregnated on 1 g of the modified support. The impregnation of the active metals was repeated so that the total active metal loading was 20 wt. %, with 75 mol. % Co and 25 mol. % Sn. The drying and calcining of Example A was repeated for this catalyst material.

Example J

Comparative

Preparation of 25 Mol. % Cobalt and 75 Mol. % Tin on Silica-Calcium Metasilicate (10 Wt. %) Support The modified support containing calcium metasilicate of Example G was used. A stock solution of 0.5 $g_{salt}$/mL, of Co(NO$_3$)$_2$.6H$_2$O (Alfa Aesar) in 8M nitric acid was prepared. A stock solution of 0.25 $g_{salt}$/mL, of Sn in 8M nitric acid was prepared with SnC$_4$H$_4$O$_6$.xH$_2$O (Alfa Aesar). 193.05 µL of the stock cobalt solution, 1060.4 µL of the stock tin solution and 66.55 µL of nitric acid was prepared and 1200 µL of this mixture was impregnated on 1 g of the modified support. The impregnation of the active metals was repeated so that the total active metal loading was 20 wt. %, with 25 mol. % Co and 75 mol. % Sn. The drying and calcining of Example A was repeated for this catalyst material.

Example K

Preparation of 50 Mol. % Cobalt and 50 Mol. % Tin with Platinum on Silica

The catalyst of Example A was used. Pt(NO$_3$)$_2$ (Sigma Aldrich) was added to the support prior to drying and calcining. There were different amounts of platinum used; 0.2 wt. %, 0.4 wt. %, and 0.6 wt. %.

Example L

Preparation of 50 Mol. % Cobalt and 50 Mol. % Tin with Platinum on Silica-Calcium Metasilicate (10 Wt. %) Support The catalyst of Example G was used. Pt(NO$_3$)$_2$ (Sigma Aldrich) was added to the support prior to drying and calcining. There were different amounts of platinum used; 0.2 wt. %, 0.4 wt. %, and 0.6 wt. %.

Gas Chromatographic (GC) Analysis of the Products

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify: Acetaldehyde, Ethanol, Acetone, Methyl acetate, Vinyl acetate, Ethyl acetate, Acetic acid, Ethylene glycol diacetate, Ethylene glycol, Ethylidene diacetate, and Paraldehyde. The middle channel was equipped with a TCD and Porabond Q column and was used to quantify: CO$_2$, Ethylene, and Ethane. The back channel was equipped with a TCD and Porabond Q column and was used to quantify: Helium, Hydrogen, Nitrogen, Methane, and Carbon monoxide.

An acetic acid feed liquid was evaporated and charged to the reactor along with hydrogen and helium as a carrier gas with an average combined gas hourly space velocity (GHSV) of about 2430 hr$^{-1}$ at a temperature of about 250° C. and pressure of 2500 kPa. A portion of the vapor effluent was passed through a gas chromatograph for analysis of the contents of the effluents.

Example 1

Co/Sn Compared to Co

The catalysts of Examples A and B were tested against the catalyst of Examples C and D. The conversion of acetic acid and selectivities are reported in Table 2 at 20 and 60 TOS (time on stream—in hours).

TABLE 2

|  | HOAc conversion (%) | | Selectivity (%) | | | | | |
|  | | | EtOH | | EtOAc | | CH$_4$ | |
|  | TOS | | | | | | | |
|  | 20 | 60 | 20 | 60 | 20 | 60 | 20 | 60 |
| Co—Sn | | | | | | | | |
| Ex. A | 70 | 60 | 50 | 56 | 26 | 33 | 1 | 1 |
| Ex. B | 67 | 57 | 21 | 18 | 80 | 75 | 1 | 2 |
| Co | | | | | | | | |
| Ex. C | 20 | 7 | 63 | 28 | 22 | 20 | 20 | 30 |
| Ex. D | 60 | 7 | 20 | 4 | 80 | 76 | 24 | 27 |

Example 2

Co/Sn Compared to Co/Cu

The catalysts of Examples A and B were tested against the catalyst of Examples E and F. The conversion of acetic acid and selectivities are reported in Table 3 at 20 and 60 TOS (time on stream—in hours).

TABLE 3

|  | HOAc conversion (%) | | Selectivity (%) | | | | | |
|  | | | EtOH | | EtOAc | | AcH | |
| TOS | 20 | 60 | 20 | 60 | 20 | 60 | 20 | 60 |
| Ex. K (0% Pt) | 70 | 60 | 51 | 58 | 16 | 6 | 33 | 35 |
| Ex. L (0% Pt) | 71 | 59 | 60 | 64 | 10 | 4 | 29 | 32 |
| Ex. K (0.2% Pt) | 53 | 41 | 35 | 73 | 25 | 9 | 35 | 17 |
| Ex. L (0.2% Pt) | 50 | 45 | 37 | 81 | 26 | 9 | 38 | 8 |
| Ex. K (0.4% Pt) | 70 | 56 | 35 | 82 | 40 | 10 | 20 | 6 |
| Ex. L (0.4% Pt) | 59 | 68 | 46 | 84 | 30 | 10 | 23 | 6 |
| Ex. K (0.6% Pt) | 75 | 73 | 51 | 83 | 35 | 10 | 15 | 5 |
| Ex. L (0.6% Pt) | 66 | 78 | 50 | 81 | 32 | 13 | 19 | 5 |

Example 3

Co/Sn Molar Ratio

The catalysts of Examples A and G were tested against the catalyst of Examples H, I, and J. The conversion of acetic acid and selectivities are reported in Table 4 at 20 and 60 TOS (time on stream—in hours).

TABLE 4

|  | HOAc conversion (%) | | Selectivity (%) | | | | | |
|  | | | EtOH | | EtOAc | | AcH | |
| TOS | 20 | 60 | 20 | 60 | 20 | 60 | 20 | 60 |
| Rh | 81 | 78 | 58 | 75 | 20 | 9 | 18 | 15 |
| Pd | 60 | 50 | 35 | 56 | 16 | 6 | 38 | 32 |
| Au | 80 | 65 | 25 | 55 | 35 | 8 | 28 | 33 |
| Ru | 65 | 50 | 45 | 63 | 17 | 8 | 31 | 25 |
| Ir | 60 | 50 | 50 | 68 | 15 | 6 | 33 | 24 |
| None | 70 | 60 | 50 | 57 | 15 | 6 | 28 | 33 |

Example 4

Co/Sn with Pt

The catalysts of Examples K and L were tested. The conversion of acetic acid and selectivities are reported in Table 5 at 20 and 60 TOS (time on stream—in hours).

TABLE 5

|  | HOAc conversion (%) | | Selectivity (%) | | | | | |
|  | | | EtOH | | EtOAc | | AcH | |
|  | TOS | | | | | | | |
|  | 20 | 60 | 20 | 60 | 20 | 60 | 20 | 60 |
| 0% Pt | | | | | | | | |
| Ex. K | 70 | 60 | 51 | 58 | 16 | 6 | 33 | 35 |
| Ex. L | 71 | 59 | 60 | 64 | 10 | 4 | 29 | 32 |
| 0.2% Pt | | | | | | | | |
| Ex. K | 53 | 41 | 35 | 73 | 25 | 9 | 35 | 17 |
| Ex. L | 50 | 45 | 37 | 81 | 26 | 9 | 38 | 8 |
| 0.4% Pt | | | | | | | | |
| Ex. K | 70 | 56 | 35 | 82 | 40 | 10 | 20 | 6 |
| Ex. L | 59 | 68 | 46 | 84 | 30 | 10 | 23 | 6 |
| 0.6% Pt | | | | | | | | |
| Ex. K | 75 | 73 | 51 | 83 | 35 | 10 | 15 | 5 |
| Ex. L | 66 | 78 | 50 | 81 | 32 | 13 | 19 | 5 |

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the above descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A hydrogenation catalyst for reducing alkanoic acids to alcohols, the catalyst comprising from 10 to 20 wt. % of active metals on a support, wherein the active metals consist essentially of cobalt and tin; wherein the active metals are present in a molar ratio from 1.9:1 to 1:1.9 cobalt to tin, and wherein the catalyst does not contain copper or zinc.

2. The catalyst of claim 1, wherein the active metals are present in a substantially equal molar ratio of cobalt to tin.

3. The catalyst of claim 2, wherein the substantially equal molar ratio is from 1.2:1 to 1:1.2.

4. The catalyst of claim 1, wherein the support is selected from the group consisting of silica, silica/alumina, calcium metasilicate, pyrogenic silica, high purity silica, and mixtures thereof.

5. The catalyst of claim 1, wherein the support further comprises a support modifier.

6. The catalyst of claim 5, wherein the support modifier is present in an amount from 0.1 wt. % to 50 wt. %.

7. The catalyst of claim 5, wherein the support modifier is selected from the group consisting of (i) alkaline earth metal oxides, (ii) alkali metal oxides, (iii) alkaline earth metal metasilicates, (iv) alkali metal metasilicates, (v) (Group IIIB metal oxides, (vi) Group IIIB metal metasilicates, and mixtures thereof.

8. The catalyst of claim 5, wherein the support modifier is calcium metasilicate.

9. The catalyst of claim 5, wherein the support modifier is selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $Nb_2O_5$, $MnO_2$, $Co_2O_3$, and $Bi_2O_3$.

10. A hydrogenation catalyst for reducing alkanoic acids to alcohols, the catalyst comprising from 10 to 20 wt. % of active metals on a support, wherein the active metals consist essentially of a substantially equal molar ratio of cobalt to tin, and wherein the catalyst does not contain copper or zinc.

11. The catalyst of claim 10, wherein the substantially equal molar ratio is from 1.2:1 to 1:1.2.

* * * * *